US00PP28706P3

(12) United States Plant Patent
Giesen

(10) Patent No.: US PP28,706 P3
(45) Date of Patent: Nov. 28, 2017

(54) *DAHLIA* PLANT NAMED 'DAHZ0001'

(50) Latin Name: ***Dahlia* hybrid Cav.**
Varietal Denomination: DAHZ0001

(71) Applicant: SYNGENTA PARTICIPATIONS AG, Basel (CH)

(72) Inventor: Eric Giesen, Andijk (NL)

(73) Assignee: Syngenta Participations AG, Basel (CH)

( * ) Notice: Subject to any disclaimer, the term of this patent is extended or adjusted under 35 U.S.C. 154(b) by 130 days.

(21) Appl. No.: 14/757,056

(22) Filed: Nov. 13, 2015

(65) Prior Publication Data

US 2016/0165786 P1 Jun. 9, 2016

Related U.S. Application Data

(60) Provisional application No. 62/088,968, filed on Dec. 8, 2014.

(51) Int. Cl.
*A01H 5/02* (2006.01)

(52) U.S. Cl.
USPC ..... Plt./321

(58) Field of Classification Search
USPC ..... Plt./263.1, 321
See application file for complete search history.

*Primary Examiner* — Susan McCormick Ewoldt
*Assistant Examiner* — Karen Redden
(74) *Attorney, Agent, or Firm* — Dale Skalla

(57) ABSTRACT

A new *Dahlia* plant named 'DAHZ0001', particularly distinguished by the large yellow double-type flowers, full and compact plant habit with excellent branching, medium green foliage, and good floriferiousness.

1 Drawing Sheet

Latin name of the genus and species of the plant claimed: *Dahlia* hybrid Cay.

Varietal denomination: 'DAHZ0001'.

BACKGROUND OF THE NEW PLANT

The present invention comprises a new *Dahlia*, botanically known as *Dahlia* hybrid and hereinafter referred to by the variety name 'DAHZ0001'.

'DAHZ0001' is a product of a planned breeding program. The new cultivar 'DAHZ0001' has large yellow double-type flowers, full and compact plant habit with excellent branching, medium green foliage, and good floriferousness.

'DAHZ0001' originates from a sibling cross hybridization in a controlled breeding program in Andijk, Netherlands. The pollinations were made in August 2007.

The female parent was an unpatented, proprietary hybrid seedling identified as 'DO6-262-1', having pink color, larger flowers and a smaller plant size than 'DAHZ0001'.

The male parent of 'DAHZ0001' was an unpatented, proprietary plant identified as 'DO6-265-1', with yellow flower, smaller flower size, smaller leaves, and more freely branching plant habit than 'DAHZ0001'.

The resulting the seed sown in November 2007, and 'DAHZ0001' was selected as one flowering plant within the progeny of the stated cross in February 2008 in a greenhouse in Andijk, Netherlands.

The first act of asexual reproduction of 'DAHZ0001' was accomplished when vegetative cuttings were propagated from the initial selection in March 2008 in a controlled environment in Andijk, Netherlands.

BRIEF SUMMARY OF INVENTION

Horticultural examination of plants grown from cuttings of the plant initiated in April 2008 in Andijk, Netherlands, and continuing thereafter, has demonstrated that the combination of characteristics as herein disclosed for 'DAHZ0001' are firmly fixed and are retained through successive generations of asexual reproduction.

'DAHZ0001' has not been observed under all possible environmental conditions. The phenotype may vary significantly with variations in environment such as temperature, light intensity and day length.

A Plant Breeder's Right for this cultivar was applied for in the European Community Plant Variety Office (CPVO) on Apr. 22, 2014, No. 2014/1052. 'DAHZ0001' has not been made publicly available more than one year prior to the filing of this application.

The following traits have been repeatedly observed and are determined to be basic characteristics of the new variety. The combination of these characteristics distinguishes this *Dahlia* as a new and distinct variety.

BRIEF DESCRIPTION OF THE PHOTOGRAPHS

Figure 1:
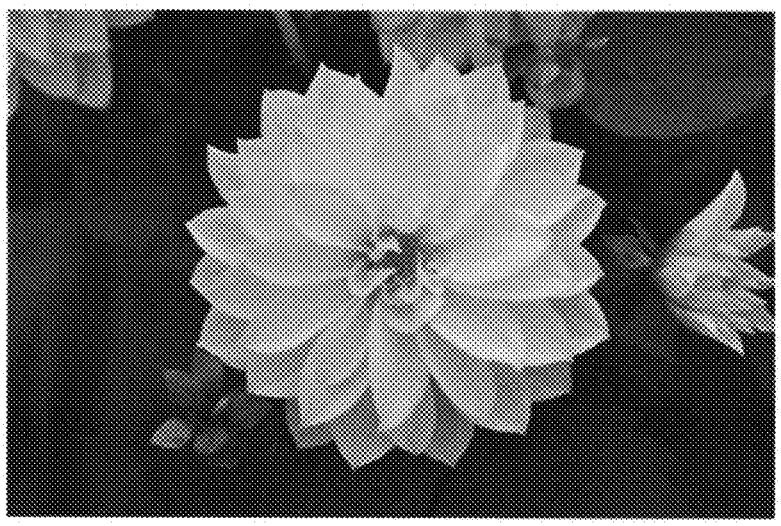
Figure 2:
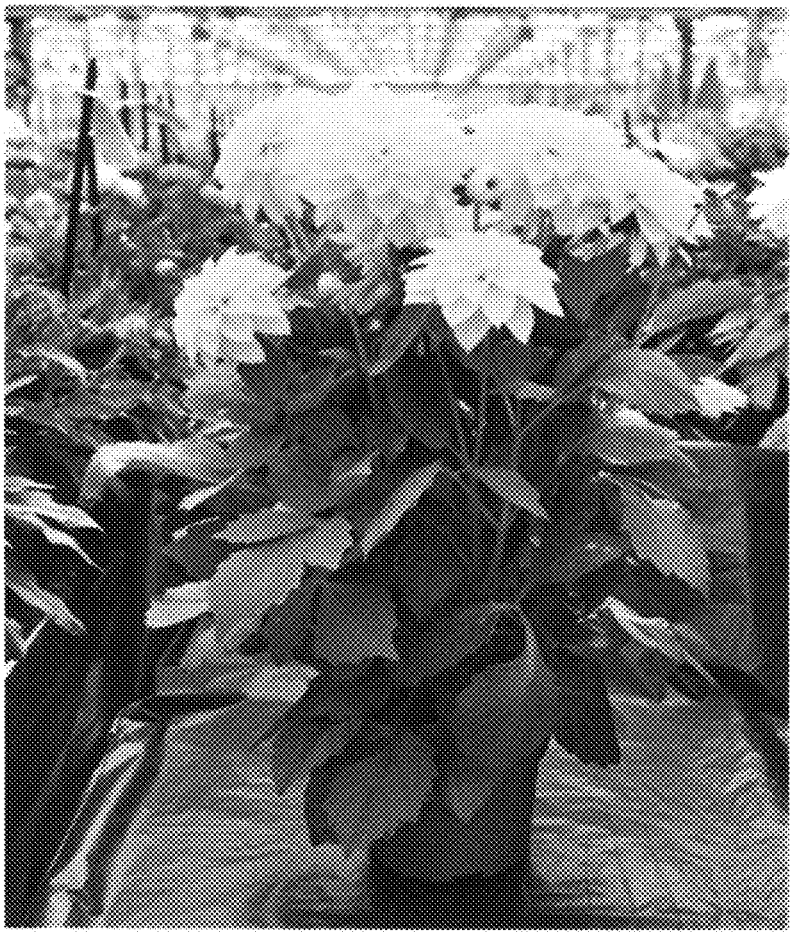

The accompanying photographic drawings show typical flower and foliage characteristics of 'DAHZ0001' with colors being as true as possible with an illustration of this type. The photographic drawings show in FIG. 1 a close-up of the flowers and FIG. 2 a flowering potted plant of the new variety.

DETAILED BOTANICAL DESCRIPTION

The plant descriptions and measurements were taken in Enkhuizen, The Netherlands, on the $4^{th}$ of September, from 14 week old plants that were growing outdoors in the trial field.

The aforementioned photographs were taken at the same time in April 2012 in Andijk, Netherlands. The potted plants were growing on benches in a greenhouse. They were about 12 weeks of age.

Color references are made to The Royal Horticultural Society Colour Chart (R.H.S.) 2001.

TABLE 1

DIFFERENCES BETWEEN THE NEW VARIETY 'DAHZ0001' AND A SIMILAR VARIETY

| | 'DAHZ0001' | 'GALLERY CEZANNE' U.S. Plant Pat. No. 10,511 |
|---|---|---|
| Overall flower color: | Yellow | Yellow |
| Plant habit: | More vigorous | Smaller plant |
| Flower, position: | Above foliage | Some flowers under foliage |
| Number of whorls of ray florets: | More, 9 to 10 | Fewer, 7 to 8 |
| Flower type: | Daisy-eyed double | Double |

Plant:

*Form, growth and habit.*—Semi-upright, tight and compact; freely branching.

*Plant height.*—26 cm.

*Plant height (inflorescence included).*—37 cm.

*Plant width.*—39-43 cm.

*Garden performance and tolerance to weather.*—Good.

*Cultivation time to flowering.*—About 9-12 weeks.

Roots:

*Number of days to initiate and develop roots.*—About 21-28 days at about 21 degrees C.

*Type.*—Fine, fibrous, free branching.

*Color.*—RHS N155B but whiter.

Foliage:

*Arrangement.*—Opposite, single, simple and sometimes pinnate.

*Immature, leaf color, upper surface.*—Between RHS 137A.

*Lower surface.*—RHS 138C to RHS 138D but slightly more greyish.

*Mature, leaf color, upper surface.*—RHS 147A.

*Lower surface.*—RHS 138C, but slightly more greyish.

*Type.*—Mostly simple, some are pinnate.

*Length.*—12 cm, including petiole.

*Width.*—8 cm.

*Shape.*—Ovate to deltoid for the pinnate.

*Base shape.*—Pinnate leaves are truncate, simple leaves are acute.

*Apex shape.*—Acute to obtuse.

*Margin.*—Dentate.

*Texture, upper surface.*—Little hairy on the edges, slightly glossy.

*Texture, lower surface.*—Some lonely hair on the main vein.

*Venation color, upper surface.*—RHS 143C.

*Venation color, lower surface.*—RHS 144D.

*Petiole color.*—RHS 144C.

*Petiole length.*—1-4 cm.

*Diameter of petiole.*—0.3 cm at the mid-section.

*Texture.*—Glabrous.

Stem:

*Average quantity of main branches per plant.*—About 5 to 6, each with 3 finer branches on average.

*Color of stem.*—RHS 144B-C.

*Length of stem.*—21 cm.

*Diameter.*—0.6 cm at the mid-section.

*Length of internodes.*—4.5-7.5 cm.

*Texture.*—Glabrous.

*Color of peduncle.*—RHS N144D.

*Length of peduncle.*—6-10 cm.

*Peduncle diameter.*—0.2-0.3 cm.

*Texture.*—Glabrous.

Inflorescence:

*Form.*—Capitulum (Compositae-type), borne terminally above the foliage.

*Blooming habit.*—Continuous throughout the growing season.

*Average quantity of inflorescences per plant.*—70, including buds.

*Average quantity of inflorescences per lateral stem.*—10-13.

*Lastingness of individual blooms on the plant.*—7-12 days.

*Fragrance.*—None.

Bud (just before opening):

*Color.*—Yellow, deeper than RHS 2A at the top, to greenish at the base: RHS 144A.

*Length.*—1.6 cm.

*Width.*—1.8 cm.

*Shape.*—Completely round to bell-shaped at unfolding of the rays.

Immature inflorescence:

*Diameter.*—About 6.1 cm.

*Color of ray florets, upper surface.*—RHS 1A.

*Lower surface.*—RHS 1A to RHS 1B.

Mature inflorescence:

*Type and shape.*—Double-type, often with a small disk visible ('daisy-eyed double').

*Diameter.*—8.5-10 cm.

*Depth.*—4 cm.

*Diameter of the disc.*—1-1.2 cm.

*Receptacle height.*—0.2 cm.

*Receptacle diameter.*—1.4-1.5 cm.

Ray florets:

*Average quantity of florets.*—About 75-80, arranged in several whorls.

*Shape.*—Broad elliptical; smallest rays around the disk are incompletely developed, curved or twisted, not flat, but often involute.

*Color of florets, upper surface.*—RHS 2A, but deeper.

*Lower surface.*—RHS 2B.

*Length.*—3.2 to 3.5 cm; smallest rays are up to 1 cm long.

*Width.*—1.5 cm, smallest rays are less than 0.5 cm wide.

*Apex shape.*—Mucronulate.

*Base shape.*—Forming a tube at the base, acute.

*Margin.*—Entire.

*Texture, upper surface.*—Papillose, glabrous.

*Lower surface.*—Papillose; single hairs along the veins.

Disc florets:

*Average quantity of florets.*—About 70-80 quantity.

*Color of florets.*—RHS 21A at the apex, RHS 12A for the lower part.

*Length.*—0.7-0.8 cm.

*Width.*—0.25 cm.

*Shape.*—Tube-shaped.

*Apex shape.*—Acute, 5-pointed.

Recptacle:

*Phyllaries.*—Arranged in 2-3 whorls, two different types of phyllaries are developed: those of the lower whorl are thicker and green in color, while the upper ones are thinner and semi-transparent.

*Phyllaries of the lower whorl.*—
*Average quantity*.—About 5-7.
*Color, upper surface*.—RHS 147A.
*Lower surface*.—RHS 147A.
*Length*.—1.0 cm.
*Width*.—0.7 cm.
*Shape*.—Ovate.
*Base shape*.—Shortly attenuate.
*Apex shape*.—Acuminate.
*Margins*.—Entire.
*Texture, upper surface*.—Glabrous.
*Texture, lower surface*.—Glabrous.
*Phyllaries of the upper whorl.*—
*Average quantity*.—About 10.
*Color, upper surface*.—RHS 154C to RHS 154D, but appear semi-transparent; RHS N144C at the base.
*Color, lower surface*.—RHS 154C to RHS 154D, but appears semi-transparent, RHS N144C at the base.
*Length*.—1.7 cm.
*Width*.—0.6 cm.
*Shape*.—Ligulate.
*Base shape*.—Fused.
*Apex shape*.—Obtuse.
*Margins*.—Entire.
*Texture, upper surface*.—Glabrous.
*Lower surface*.—Glabrous.

Reproductive organs:
Gynoecium: Present in both ray and disc florets.
*Pistil quantity*.—1 per floret.
*Length*.—0.8-0.9 cm.
*Style color*.—RHS 154B.
*Style length*.—0.5-0.6 cm.
*Stigma color*.—RHS 13B.
*Stigma shape*.—Bi-furchate (bi-lobed).
*Ovary color*.—RHS 145C.
Androecium: Present in disc florets only.
*Stamens quantity*.—5 united per floret.
*Color of filaments*.—RHS 150D.
*Length filaments*.—0.3 cm.
*Anther color*.—RHS 17B.
*Anther length*.—0.4 cm.
*Color of pollen*.—RHS 17A.
*Pollen amount*.—Very moderate.
*Fertility/seed set*.—Not observed on this hybrid.
Disease/pest resistance: Disease resistance or susceptibility has not been observed on this hybrid.

What is claimed is:

1. A new and distinct variety of *Dahlia* plant named 'DAHZ0001', substantially as illustrated and described herein.

* * * * *